(12) United States Patent
Blass et al.

(10) Patent No.: US 8,435,547 B2
(45) Date of Patent: *May 7, 2013

(54) CREAM FOR STIMULATING MITOCHONDRIAL ACTIVITY IN THE SKIN

(75) Inventors: John P. Blass, New York, NY (US); Loretta Pratt, Thornton, PA (US); Steven Cosentino, Rye, NY (US)

(73) Assignee: John P. Blass, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/512,771

(22) Filed: Aug. 30, 2006

(65) Prior Publication Data

US 2008/0057088 A1  Mar. 6, 2008

(51) Int. Cl.
*A61K 8/37* (2006.01)
*A61K 8/00* (2006.01)
*A61K 8/368* (2006.01)

(52) U.S. Cl.
USPC ............................................ 424/401; 424/45

(58) Field of Classification Search .................. 424/401, 424/45
See application file for complete search history.

(56) References Cited

U.S. PATENT DOCUMENTS

| | | | |
|---|---|---|---|
| 5,395,822 A | 3/1995 | Izumi et al. | |
| 5,505,937 A | 4/1996 | Castrogiovanni et al. | |
| 5,686,489 A | 11/1997 | Yu et al. | |
| 5,853,742 A * | 12/1998 | Bartolone et al. | 424/401 |
| 6,261,603 B1 | 7/2001 | McElwain et al. | |
| 6,270,780 B1 | 8/2001 | Carson et al. | |
| 6,300,377 B1 * | 10/2001 | Chopra | 514/715 |
| 6,328,987 B1 | 12/2001 | Marini | |
| 6,358,517 B1 | 3/2002 | Pillai et al. | |
| 6,372,791 B1 | 4/2002 | Shapiro et al. | |
| 6,399,046 B1 | 6/2002 | Schönrock et al. | |
| 6,537,969 B1 | 3/2003 | Blass | |
| 6,846,812 B2 | 1/2005 | Dalko et al. | |
| 6,872,401 B2 | 3/2005 | Seyler et al. | |
| 6,962,712 B2 | 11/2005 | Breton et al. | |
| 7,368,144 B2 * | 5/2008 | Lecoupeau et al. | 426/655 |
| 2003/0007961 A1 * | 1/2003 | Wilburn | 424/94.4 |
| 2004/0258647 A1 * | 12/2004 | Ruppert et al. | 424/70.16 |

OTHER PUBLICATIONS

International Search Report for Application No. PCT/US 06/37157.
International Search Report for Application No. PCT/US 06/37157, Jun. 5, 2005.

* cited by examiner

*Primary Examiner* — Janet Epps-Smith
*Assistant Examiner* — Courtney Brown
(74) *Attorney, Agent, or Firm* — Pearl Cohen Zedek Latzer, LLP

(57) ABSTRACT

A skin care composition is useful for augmenting cellular metabolism in skin cells and thereby enhancing the regulation of intracellular signaling. The composition comprises a primer for skin cell mitochondrial function, such as a Krebs cycle intermediate, a precursor of a Krebs cycle intermediate, salts or esters thereof, or combinations thereof. The composition may also include antioxidants for free radical regulation and a pharmaceutically acceptable topical vehicle, such as an emollient base for skin health. A method for stimulating the mitochondrial activity of skin cells comprises administering to the skin of a person in need thereof a composition as described herein.

23 Claims, No Drawings

CREAM FOR STIMULATING MITOCHONDRIAL ACTIVITY IN THE SKIN

FIELD OF THE INVENTION

The present invention relates to a skin rejuvenation preparation that is beneficial for dry, scarred, damaged or aging skin by promoting the metabolism of treated skin cells.

BACKGROUND OF THE INVENTION

The human skin consists of two major layers, the bottom thicker layer called the dermis and the top thinner layer called the epidermis. The epidermis is composed principally of three types of cells, the keratinocytes, the melanocytes and the cells of Langerhans. The epidermis cells are generated on the bottom of the epidermis and work their way to the top, where they eventually flake or slough off. This epidermis "turnover" takes approximately 2-4 weeks and often twice as long in people as they age.

The dermis is the layer that provides strength, elasticity and the thickness to the skin, and provides the epidermis with a solid support and is also its nutritive element. The dermis is composed mainly of fibroblasts and of an extracellular matrix itself composed principally of collagen, elastin and a substance called ground substance, which are compounds synthesized by the fibroblasts. The dermis is also composed of leukocytes, mastocytes or tissue macrophages, and blood vessels and nerve fibers pass through it. The dermis contains biologically young cells, including stem cells, which can grow out to form biologically younger skin under appropriate conditions. This possibility underlies many standard treatments in the field of dermatology including the various forms of mechanical, chemical and laser dermabrasion.

With aging, the thickness of the dermal layer is reduced, which is believed to be at least partially responsible for the formation of wrinkles in aging skin. In addition, the decreased rate of cellular turnover in the epidermis results in dull, dry and rough skin. The passage of time is also reflected by a slackening of tissue, a loss of cutaneous elasticity, a leathery or dry appearance and by the yellowing and loss of radiance of the skin. The aging process also results in a reduction in cells and in blood supply, and a flattening in the junction between the dermis and epidermis.

Although controversy exists about the part of the cell that is the "pacemaker" for aging, most scientific opinion favors the mitochondrion, which is also involved in the regulation of the metabolism of free radicals. These compounds, also called "reactive oxygen species" (ROS), are important signals regulating cell metabolism and function in a number of ways, including their actions on the "transcription factors" that are a major mechanism for control of gene expression. Unfortunately, treatment with "free radical quenchers" such as vitamin E or vitamin C or the grape skin ingredient resveratrol, have generally had minimal or no beneficial effects in the relevant age-related conditions, including Alzheimer disease.

Treatments designed to prolong or promote youthful appearance of skin include topical applications of cosmetic preparations, lotions and moisturizers. Many skin care compositions have been created to treat wrinkles and fine lines and restore the youthful appearance of skin, and most of these are intended only to improve the skin's surface characteristics, for example, to minimize environmental effects and stress on the skin, improve texture, firmness and elasticity, counteract dryness, smooth out wrinkles, minimize age spots, improve color, and increase moisture content of the skin. However, none of these focus on the underlying age-related changes in mitochondrial metabolism that underlie alterations in ROS.

Many such skin compositions have been made with different ingredients to promote the health of skin. For example, U.S. Pat. No. 5,686,489 (Yu) discussed methods of treating aging-related skin conditions by topically applying to the skin an alpha hydroxyacid ester, and U.S. Pat. No. 6,328,987 (Marini) discuss improving the appearance of aged or damaged skin by topically applying compositions containing alpha interferon.

Other skin and cosmetic compositions incorporate antioxidants in order to improve the appearance of wrinkled, lined, dry, flaky, aged or photodamaged skin and improve skin thickness, elasticity, flexibility, radiance, glow and plumpness. For example, the compositions disclosed in U.S. Pat. No. 6,270,780 (Carson et al.) and U.S. Pat. No. 6,358,517 (Pillai et al.) incorporate resveratrol as a primary ingredient in addition to a cosmetically acceptable vehicle. Carson et al. combine hydroxyl acid with the resveratrol, and Pillai et al. combine a retinol, namely retinoic acid, retinol or retinyl acetate, with the resveratrol. In addition, U.S. Pat. No. 6,399,046 (Schenrock et al.) discusses the use of catechins or gallic esters of catechins, such as in extracts from green tea, for intensifying natural skin tanning or for stimulating melanogenesis in human skin. While some of these formulations include antioxidants, such as resveratrol, none include chemicals that act to restore mitochondrial function in the skin cells.

In order to survive and work properly, skin cells, like all eukaryotic cells, require energy, which is derived mostly from the diet. Food gets successively digested and metabolized to simple molecular entities that the individual cells, using their mitochondria, can convert into energy. However, because the mitochondrial membranes are permeable only to certain molecules, carbohydrates and certain amino acids have to be broken down in the cytosol into pyruvate, while fatty acids can be absorbed by the mitochondria with the help of a specific carrier, L-carnitine.

During normal operation of the catabolic process in body cells, energy is harvested and subsequently stored in a readily available form, namely, the phosphate bonds of adenosine triphosphate ("ATP"). When energy is required for anabolic processes, a phosphate bond of ATP is broken to yield energy for driving anabolic reactions and adenosine diphosphate ("ADP") is regenerated. The process of catabolism involves the breakdown of proteins, polysaccharides, and lipids inside the mitochondria. Proteins are broken into smaller peptides and constituent amino acids, polysaccharides and disaccharides are broken down into their monosaccharide constituents, and lipids are broken down into glycerol and the fatty acid constituents. These compounds are further broken down into even smaller compounds, principally, two-carbon acetyl groups.

The two-carbon acetyl group, an essential component in the catabolic process, is introduced into the Krebs tricarboxylic acid cycle ("Krebs cycle") via acetyl coenzyme A. The acetyl group serves as a carbon source for the final stages of catabolism. The Krebs cycle and an accompanying electron transport system involve a series of enzymatically controlled reactions that enable complete oxidation of the two-carbon acetyl group to form carbon dioxide and water. As is well known, acetyl groups are introduced into the Krebs cycle by bonding to oxaloacetic acid to form citric acid. During subsequent steps of the Krebs cycle, citric acid is converted into aconitic acid and then into isocitric acid. As isocitric acid is converted into ketoglutaric acid, one carbon atom is completely oxidized to carbon dioxide. As ketoglutaric acid is converted into succinic acid, a second carbon atom is completely oxidized to carbon dioxide. During the remaining steps, succinic acid is converted into fumaric acid, fumaric acid is converted into malic acid, and malic acid is converted into oxaloacetic acid. Each complete turn of the Krebs cycle harvests the energy of the acetyl group to yield one molecule of ATP, three molecules of nicotinamide adenine dinucleotide ("NADH"), and one molecule of flavin adenine dinucleotide $FADH_2$. The NADH and $FADH_2$ are subsequently used as electron donors in the electron transport system to yield additional molecules of ATP.

Critically, the electrons ("reducing equivalents") generated in the Krebs tricarboxylic acid cycle are quantitatively the primary source both of electrons for formation of free radicals and of reducing equivalents to remove ("quench") free radicals. Thus, facilitation of a normal Krebs cycle is expected to facilitate normalization of free radical (ROS) metabolism and signaling.

The Krebs cycle also generates carbon dioxide ($CO_2$) and electron-transporters NADH and $FADH_2$ that feed the electron transport chain or respiratory chain reducing oxygen ($O_2$) into water ($H_2O$) and generating a proton gradient. This proton gradient creates a natural flow back into the mitochondrial matrix through a protein complex that produces ATP, the principle cellular energy store. For example, ATP is directly used in biochemical synthesis, signal transduction, cell movement, cellular division, and ion pumping.

The Krebs cycle and the accompanying electron transport system occur in the cell mitochondria, which are present in different types of cells in varying numbers depending upon the cellular energy requirements. For example, neuronal and cardiac muscle cells have high numbers of mitochondria because they have extremely high energy requirements. Because of their high energy requirements, these types of cells are particularly vulnerable to a breakdown of the catabolic pathways or otherwise defective intracellular energy metabolism, leading to neurodegenerative disorders or conditions such as Alzheimer's Disease, Parkinson's Disease and Huntington's Disease.

The administration of agents that improve energy metabolism, and possibly prevent cell death, has been suggested for the treatment of disorders characterized by energy-deficient cells. One approach to augmenting the energy level of energy-deficient cells (i.e., as a result of hypoxia or hypoglycemia) involves the administration of pyruvate, which is later converted to acetate during normal metabolism. According to U.S. Pat. No. 5,395,822 (Izumi et al.), the administration of pyruvate to an animal before or after an ischemic event (i.e., which produces a state of hypoxia or hypoglycemia) is sufficient to prevent neuronal degradation that normally is associated with the ischemic event.

In U.S. Pat. No. 6,537,969, which is incorporated herein by reference, the present inventor disclosed a pharmaceutical composition to improve cerebral function in an individual having a disorder involving impaired mitochondrial function, such as age-related conditions, e.g., Alzheimer's Disease, where brain mitochondrial metabolism has been robustly shown to be impaired. That composition was designed to ameliorate the changes in mitochondrial metabolism that are believed to underlie the changes in ROS metabolism and signaling as a treatment for such systemic diseases.

U.S. Pat. No. 6,372,791 (Shapiro et al.) has suggested topically administering carnitine or a therapeutically acceptable salt or ester thereof and pyruvic acid or a therapeutically acceptable salt or ester thereof in order to increase metabolic activity in the skin (e.g., the production of ATP in the skin cells or the increase of mitochondrial activity in the skin cell), promote energy production or the uptake of oxygen into the skin (e.g., increasing the amount of oxygen stored in the skin cells or increasing the rate by which oxygen is taken in by the skin cells), and promote the utilization of oxygen ($O_2$) in the skin (e.g., increasing the amount of oxygen utilized, e.g., converted to $CO_2$ or other compounds, in the skin cells or increasing the rate by which oxygen is utilized by the skin cells).

It is desirable to provide for healthier, "biologically younger" skin, by enhancing skin firmness and elasticity, evening skin tone/texture, making skin more radiant, enhancing skin glow, and enhancing skin barrier function through the administration to the skin of substances that promote the normal mitochondrial activity of the skin cells.

It is desirable to provide a skin care composition that ameliorates the changes in mitochondrial metabolism in skin cells and that restores mitochondrial function to skin cells to make skin "younger".

SUMMARY OF THE INVENTION

The present invention features novel cosmetic skin care compositions that treat wrinkles and fine lines, firming skin tissue and reviving the radiance of the skin through administration of mitochondrial substrates that have not been previously disclosed for use in treatment of the skin. The present invention is directed to a pharmaceutical composition for use in treatment of the skin by facilitating mitochondrial metabolism and specifically the Krebs tricarboxylic acid cycle, thus restoring the ability of the cells to regulate free radical metabolism and therefore free radical signaling, thereby favoring the metabolism of biologically younger skin cells and minimizing the metabolic consequences of aging processes in older skin cells. The composition described herein is an adaptation to the skin cells of the inventor's approach in U.S. Pat. No. 6,537,969, discussed above.

Compositions of the instant invention may be applied directly to the skin for treatment of aging related skin changes including pigmented and non-pigmented age spots, skin lines, scars, wrinkles and photoaging with minimal external activation or stimulation of the skin. By positively affecting changes in the dermis, visible changes in the skin will occur. For example, wrinkles and skin lines will be visibly reduced or eradicated, the skin will appear plumper and fuller, and the skin thus will attain a younger or more youthful appearance.

In addition, whereas the rate of epidermis "turnover" decreases with age, it is believed that the skin care composition of the present invention affects epidermal cellular metabolism and stimulates cellular turnover to return to a more youthful rate. The result is skin that is smoother, has better clarity and is less dry and dull, which can be attributed to an epidermal effect. Another possible epidermal effect of the inventive composition is improvement in pigmentary abnormalities.

The skin care composition of the present invention is useful for augmenting cellular metabolism in skin cells. It is believed that application of the inventive skin care composition enhances the ability of skin cells to regulate themselves in a healthy state, i.e., to maintain homeostasis, in part by enhancing mitochondrial function by augmenting operation of the Krebs cycle. Applying a Krebs cycle intermediate or the precursor of a Krebs cycle intermediate to skin cells increases the concentration of the particular Krebs cycle intermediate available at the mitochondrial level in those skin cells, and extensive, robust biochemical data accumulated over decades indicate that this is necessary for optimal activity of the Krebs cycle (i.e., it has a priming effect), because a four carbon intermediate is needed in order for the two-carbon derivatives of glucose and other substrates to enter the Krebs cycle. Specifically, the two-carbon acetyl group must combine with the four-carbon oxaloacetate to form citrate in order for the Krebs cycle to continue. Malate is in equilibrium with oxaloacetate, and other Krebs cycle intermediates are readily converted to malate and oxaloacetate. The conversion of succinate and fumarate to malate and oxaloacetate is particularly rapid. Metabolically compromised cells tend to utilize Krebs cycle intermediates for the direct generation of electrons (reducing equivalents), as discussed above. More specifically, they utilize the intermediates to generate electrons that then generate ATP through electron transport. While utilizing the intermediates provides an immediate source of electrons, doing so compromises the subsequent activity of the Krebs cycle. Accordingly, application of the inventive skin care compositions can be predicted, therefore, to prime the Krebs cycle in the skin cells so that it again operates efficiently.

The theory behind the ingredients is fourfold. First, the quantity of reactive oxygen species and of "quenchers" of oxidation produced by the human body per day is far larger than the amount of antioxidant than can be safely ingested or put on the skin. The rate of production of ROS per person per day can be calculated from normal oxygen ($O_2$) consumption. In normal resting humans that is about 40 ml/min/kg body weight (it is higher in athletes or during exercise), which works out to approximately 166 moles of $O_2$ per day per 70 kg person. Estimating conservatively that only 2% of that $O_2$ is utilized to make ROS implies that the normal resting human makes about 6 moles of ROS/day. For the antioxidant vitamin E (m.w. 430.7), toxicity is evident at doses above 1 gm/day. Therefore, the maximum proportion of the body's daily production of ROS that can be neutralized ("quenched") by acceptable amounts of oral vitamin E is approximately 0.1%. By way of reference, quenching 0.1% of the ROS produced per day through drinking red wine would require a person to ingest about 100 liters of a red wine rich in resveratrol (e.g., certain Pinot Noirs). Neither that amount of vitamin E nor that amount of red wine is consistent with health—or probably even feasible in ordinary human beings. Free radical quenchers can be "recycled," but doing so requires reducing equivalents and quantitatively requires reducing equivalents generated in the mitochondria via the Krebs cycle and then transferred to other biochemical intermediates, such as reduced glutathione and reduced lipoic acid. A major aim of the preparations described in this application, as well as in U.S. Pat. No. 6,537,969, is the improved availability of such reducing equivalents.

Second, the aim of treatment with the preparation described herein is to help the body regulate its own metabolic state rather than to "repair oxidative damage" per se. Although much interest has been focused on "free radical damage" to macromolecules (nucleic acids, proteins, and lipids in membranes) by ROS and related species, the actual amount of such damage is small under physiological circumstances—perhaps 0.01-0.1% of the molecules involved, even in disease (for instance, DNA in the brain of an Alzheimer's patient). That low quantity is unlikely to have much physiological effect, because of biological mechanisms to replace and repair the damaged molecules. Even for nuclear DNA, biological mechanisms operate to "excise" errors induced by ROS. Even for mitochondrial DNA (mtDNA), replication of normal mtDNA and replication of mitochondria containing normal mtDNA lead to a "threshold effect," which requires that a high proportion of mtDNA be damaged before any physiologically and clinically effects manifest themselves. (These effects are most striking when the damaged ("mutant") mtDNA is inherited and is, therefore, the sole mtDNA species present in the affected cells.) Physiologically, the more important action of reactive oxygen species is as information molecules. The amount of destruction they cause is less significant than their role in dysregulating cell biology, even in disease. The Nobel Prize winning work of Dr. Ferid Murad showed that free radicals (specifically, the free radical NO) have direct and important effects on modifying the properties of important physiological functions. (Murad showed, among other things, that the free radical NO is a potent "relaxing factor" for blood vessels. See, Turko I V, Murad F, Protein nitration in cardiovascular diseases, Pharmacol Rev., Vol. 54, No. 4, December 2002, pp. 619-34). Subsequently, extensive studies have documented that free radicals/ROS modulate the activity of transcription factors, the proteins that turn on or off the copying (transcription) of groups (cassettes) of genes.

Third, the preparation should include at least one antioxidant and preferably a "ladder" of natural antioxidants. Each ROS and each ROS quencher has its own oxidation/reduction potential, normally measured as a standard electrode potential. Use of a single antioxidant may do more harm than good, because, if it is used in concentrations high enough to be effective, it is also likely to cause imbalance among the ROS signaling compounds normally present in the cell and necessary for normal cell function. That generalization holds for vitamin E alone, resveratrol alone, the epigallocatechin gallate (EGCG) found in green tea, and other antioxidants. The current preparation, therefore, uses several antioxidants (derived from grape skins, green tea, and raw chocolate) to provide potential free radical quenchers with a variety of standard electrode potentials, in order to facilitate the skin cells' own regulation of the ROS of different standard electron potentials that these cells produce as they age.

Fourth, since blood circulation is required to support mitochondrial metabolism in the skin by providing oxygen and fuels (substrates), preferred formulations of the preparation contain a component to benefit circulation, such as flaxseed oil, sunflower oil and safflower oil, a natural vegetable oil rich in ω-3 and ω-6 unsaturated fatty acids. These fatty acids, which are also present in fish oils, are well established dietary supplements to benefit circulation and are particularly useful in people with atherosclerosis, which is common in the elderly. Since these components are fats, they will be absorbed through the skin into the relevant cells.

The skin care composition of the present invention in general comprises a primer for skin cell mitochondrial function. In preferred embodiments of the skin care composition, the primer for skin cell mitochondrial function comprises a Krebs cycle intermediate or salt or ester thereof, or a precursor of a Krebs cycle intermediate or a salt or ester thereof, or a combination of a Krebs cycle intermediate and a precursor of a Krebs cycle intermediate or salts or esters thereof.

In preferred embodiments, the Krebs cycle intermediate can be selected from the group consisting of citric acid, aconitic acid, isocitric acid, 2-ketoglutaric acid, succinic acid, fumaric acid, malic acid, oxaloacetic acid, and combinations thereof.

In further preferred embodiments, the precursor of a Krebs cycle intermediate can be selected from the group consisting of mono- and di-alkyl citrates, aconitates, isocitrates, α-ketoglutarates, succinates, fumarates, malates and oxaloacetates. The precursor of a Krebs cycle intermediate can also be selected from the group consisting of 2-keto-4-hydroxypropanol, 2,4-dihydroxybutanol, 2-keto-4-hydroxybutanol, 2,4-dihydroxybutyric acid, 2-keto-4-hydroxybutyric acid, aspartate, mono-alkyl esters of oxaloacetate, di-alkyl esters of oxaloacetate, and mixtures thereof. The precursor of a Krebs cycle intermediate can further be selected from the group consisting of dioctoyl malate, diisopropoyl malate, distearoyl malate, diethylhexyl malate, dipalmitoyl malate, and diesters of malate with other saturated, mono-unsaturated, or polyunsaturated alcohols that can be readily metabolized by skin cells to forms oxidized by skin cell mitochondria.

The skin care composition preferably also includes one or more antioxidants and more preferably a mixture of two or more antioxidants in order to facilitate the transfer or reducing equivalents (electrons) to the appropriate cellular components that participate in control of free radical (ROS) metabolism. The antioxidants can be selected from the group consisting of catechins, (−)-epicatechins, curcumin, ascorbic acid, Vitamin E, alpha-lipoic acid, α-tocopherol, dimethylamino-ethanol (DMAE), quercetin, flavonoids and mixtures thereof, and antioxidants found in green tea (including but not limited to catechins and polyphenols), antioxidants found in chocolate (including but not limited to catechins and polyphenols), antioxidants found in grape skins (including but not limited to resveratrol), and unpurified extracts of green tea, natural ("undutched") chocolate, processed chocolate, grape skins, grape juice, wine, and other natural materials rich in antioxidants.

In preferred embodiments, the skin care composition includes pyruvate, pyruvic acid, pyruvic acid ethyl ester (ethyl pyruvate), pyruvic acid methyl ester (methyl pyruvate) and mixtures thereof.

In addition, preferred embodiments of the skin case composition can contain relatively low concentrations of agents that are widely used in dermatology and cosmetics as debriding agents to remove dead skin, such as retinoic acid or other organic acids including 2-hydroxy acids or their esters.

The skin case composition also preferably comprises a vitamin, a mineral, a metabolism-enhancing compound, or a mixture thereof. In preferred embodiments, the vitamin is selected from the group consisting of Vitamin A, thiamine, riboflavin, niacin, pantothenic acid, pyridoxine derivatives, Cyanocobalamin, Vitamin C, chromium, Vitamin E, Vitamin K and mixtures thereof. In further preferred embodiments, the mineral is selected from the group consisting of calcium, magnesium, sodium, selenium, copper, potassium, zinc and mixtures thereof. In still further preferred embodiments, the metabolism-enhancing compound is selected from the group consisting of carnitine or other compounds that participate in oxidative/energy metabolism, such as L-carnitine, L-carnitine derivatives, creatine and mixtures thereof.

The skin care composition further preferably comprises a material that provides a fuel ("substrate") that can be readily metabolized by skin cells to provide a material for mitochondrial oxidative metabolism. This can include but is not limited to fatty acid esters of glycerol such as tri-, di- or mono- esters of glycerol with stearic acid, palmytic acid, or other naturally occurring fatty acids including unsaturated fatty acids such as arachodonic acid, with octanoic acid, with organic acids with one carboxyl group and carbon lengths of 10-14 carbon atoms or carbon lengths of 20 or more (either saturated or unsaturated), and with the fatty acids derived from ω-3 or ω-6 unsaturated fatty acids. They can also include esters of these fatty acids with alcohols other than glycerol, as well as esters of glycerol with dicarboxylic acids including components of the Krebs tricarboxylic acid cycle, in which either one or both carboxyl groups of the dicatboxylic acid are esterified, to either the same —OH group in a polyalcohol such as glycerol or α,β-butanediol.

The skin care composition preferably also includes a pharmaceutically acceptable topical vehicle, which in preferred embodiments is a substrate for skin health, such as an emollient base, which can include esters, fatty acids and alcohols, polyols, hydrocarbons and mixtures thereof. The fatty acids can include those described above, including ω-3 fatty acids, and ω-6 fatty acids, and the alcohols and alcohol derivatives can include saturated or unsaturated monoglycerides, diglycerides, triglycerides, fatty acids, fatty alcohols, phosphatides, sterols, fat-soluble vitamins, terpenes, and mixtures thereof. Specifically, these components can include high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, fish oil, mineral oil, petroleum jelly, squalene, isoparaffins and mixtures thereof.

The skin care can also include at least one pharmaceutically acceptable excipient, such as thickeners, powders, sunscreens, coloring agents, opacifiers, perfumes, diluents, dispersants and mixtures thereof, and can be in the form of a lotion, cream, gel, spray, pump or impregnated pad or patch.

The invention also includes a method for stimulating the mitochondrial activity of skin cells, comprising administering to the skin of a person in need thereof of a skin case composition such as described herein.

DETAILED DESCRIPTION OF THE INVENTION

One preferred ingredient of the inventive skin care composition is what is called "mitochondrial substrates", namely Krebs cycle intermediates and precursors of Krebs cycle intermediates or salts or esters thereof, or a combination of a Krebs cycle intermediate and a precursor of a Krebs cycle intermediate or salts or esters thereof, in order to promote healthy mitochondrial metabolism. (It is understood that identification of any substance herein also includes an implicit identification of the pharmaceutically acceptable salts or esters of that substance, such that use of the term "or salts or esters thereof" is included within the naming of each particular substance.)

In preferred embodiments, the skin care composition comprises a Krebs cycle intermediate. Krebs cycle intermediates are the acids or salts or esters of compounds that are utilized during the Krebs tricarboxylic acid cycle and include citric acid, aconitic acid, isocitric acid, α-ketoglutaric acid, succinic acid, fumaric acid, malic acid, oxaloacetic acid and mixtures thereof. Referring to FIG. 1, depending upon which Krebs cycle intermediate the skin care composition of the present invention contains, the composition can ultimately yield differing amounts of reducing equivalents (electrons) and of ATP. It is believed that a number of disorders involving altered oxidative metabolism include a disruption of the Krebs cycle at or prior to conversion of α-ketoglutaric acid to succinic acid. For such disorders, the pharmaceutical compositions of the present invention preferably contain a Krebs cycle intermediate such as succinic acid, fumaric acid, malic acid, oxaloacetic acid or mixtures thereof.

In further preferred embodiments, the skin care composition comprises a precursor of a Krebs cycle intermediate. Precursors of Krebs cycle intermediates are compounds that, upon administration to a subject, are converted by the body (i.e., in vivo) into a Krebs cycle intermediate. Generally, mono- and di-alkyl citrates, aconitates, isocitrates, α-ketoglutarates, succinates, fumarates, malates and oxaloacetates are desirable precursors because the ester-bonds are readily broken by the body to yield the Krebs cycle intermediate. Other ester precursors may be developed using known technology for enhancing entry of the precursor molecule into affected cells. One preferred class of precursors of Krebs cycle intermediates are compounds that are converted by the body into oxaloacetic acid or oxaloacetate, of which 2-keto-3-hydroxypropanol, 2,4-dihydroxybutan-1-ol, 2-keto-4-hydroxybutan-1-ol, 2,4-dihydroxybutyric acid, 2-keto-4-hydroxybutyric acid, aspartates, as well as the previously identified mono- and di-alkyl oxaloacetates, are exemplary. The amino acid aspartate is converted into oxaloacetic acid by the transamination reaction.

In a preferred embodiment of the invention, preferred Krebs cycle intermediates and precursors of Krebs cycle intermediates incorporated within the inventive skin care composition are malates, asparates, glutamates and succinates, preferably in the form of esters or diesters thereof. More preferred Krebs cycle intermediates and precursors of Krebs cycle intermediates of the inventive skin care composition are malates, including but not limited to dioctoyl malate, diisopropoyl malate, distearoyl malate, diethylhexyl malate, dipalmitoyl malate, and diesters of malate with other saturated, mono-unsaturated, or polyunsaturated alcohols that can be readily metabolized by skin cells to forms oxidized by skin cell mitochondria, as described above.

It should also be noted that carboxylic acids of any of these Krebs cycle intermediates and precursors of Krebs cycle intermediates, as well as tricarboxylic acids of some, such as citric acid, are known as skin irritants. As a result, these can also be incorporated into the inventive skin case composition in their unesterified forms and in small concentrations as an additional ingredient to remove (debride) dead skin.

The skin care composition of the present invention should preferably include an adjuvant for enhancing skin cell mitochondrial function (i.e., oxidative metabolism), and/or exchange of reducing equivalents between mitochondria and other cellular components. These can include antioxidants, vitamins, minerals and other metabolism-enhancing compounds.

The composition preferably includes one or more antioxidants, and more preferably a mixture of two or more antioxidants, in order to facilitate the transfer of reducing equivalents (electrons) to the appropriate cellular components that participate in control of free radical (ROS) metabolism. In certain preferred embodiments of the present invention, the antioxidants may be catechins and (−)-epicatechins (such as those that occur in green tea and chocolate) and curcumin (which occurs in curry spices such as turneric).

One of the preferred antioxidants to be included in the mixture of antioxidants with mitochondrial substrates in the inventive skin care composition is green tea or its powder, extract or derivatives. Recent research has begun to show that green tea extract, which is naturally rich in antioxidants, which help protect the body from free radicals, is linked to skin rejuvenation. For example, one study by Stephen Hsu et al., Journal of Pharmacology And Experimental Therapeutics, Vol. 306, pp. 29-34 (2003), suggest that green tea polyphenols may be used for treatment of wounds or certain skin conditions characterized by altered cellular activities or metabolism. Preferred antioxidants found in green tea or its extract are catechins or gallic esters of catechins, preferably polyphenols or catechins from the group (−)-catechin, (+)-catechin, (−)-catechin gallate, (−)-gallocatechin gallate, (+)-epicatechin, (−)-epicatechin, (−)-epicatechin gallate, (−)-epigallocatechin and (−)-epigallocatechin gallate, as set forth in U.S. Pat. No. 6,399,046 (Schenrock et al.), which is hereby incorporated by reference.

In certain preferred embodiments, chocolate is another preferred source of the antioxidants to be included with mitochondrial substrates and perhaps other antioxidants in the inventive skin care composition. Chocolate is now accepted to have additional beneficial health effects due to its contents of antioxidants. See, The Sweet Science: Dark Chocolate May Be Good For You, Harvard Health Letter, Vol. 29, No. 7 (2004); Lee K W et al., Cocoa Has More Phenolic Phytochemicals and a Higher Antioxidant Capacity Than Teas and Red Wine, J Agric Food Chem, Vol. 51, pp. 7292-95 (2003). Polyphenols are antioxidants that are found in both chocolate and red wine and have beneficial effects. See, Constant J, Alcohol, Ischemic Heart Disease and the French Paradox, Clinical Cardiology, Vol. 20, pp. 420-24 (1997). Additionally, cocoa butter, which is the vegetable fat contained in a cocoa bean and is removed from chocolate liquid by using high pressure, is a natural antioxidant that is a natural source of vitamin E and is known to clear and smooth the skin. It is not surprising, therefore, that a growing body of empirical evidence has recently begun to show that chocolate may have beneficial anti-aging properties when applied to the skin. See Dillinger et al., Food of the gods: cure for humanity? A cultural history of the medicinal and ritual use of chocolate, J Nutr., Vol. 130 (8S Suppl), August 2000, pp. 2057S-72S.

In certain preferred embodiments, resveratrol is another of the preferred antioxidants to be included in the mixture of antioxidants with mitochondrial substrates in the inventive skin care composition. Resveratrol (also known as 5-parahydroxystyryl resorcinol, or 3,4'5-stilbenetriol) is a compound found in a variety of plants. Isolation and characterization of resveratrol have been described from a variety of plants such as the roots of Japanese knotweed, from wine and grapes and from peanut plant cultures. Resveratrol, contained in red grapes and red wine in relatively high amounts, is claimed as one of the reasons for cardiovascular health in wine drinkers (i.e., "the French paradox"). In addition, resveratrol has been shown to be a potent cancer chemopreventive agent and an anti-inflammatory agent, has been reported to induce differentiation of human promyelocytic leukemia cells, and has been used as an anticancer agent against carcinogen-treated mouse skin cells in culture. In addition, as described above, resveratrol has been used for skin care or cosmetic, and Carson et al. describe resveratrol as a phytoestrogen, as inhibiting keratinocyte proliferation, as promoting differentiation of keratinocytes, as affecting melanin production by the skin cells, and as controlling skin irritation caused by alpha-hydroxy acids.

Other antioxidants that may be included in the skin care composition include without limitation ascorbic acid (Vitamin C), Vitamin E, alpha-lipoic acid, α-tocopherol, dimethylamino-ethanol (DMAE), quercetin and other flavonoids.

In general, the amount of the antioxidant, such as green tea extract, chocolate or resveratrol, in the inventive compositions can be in the range of from 0.00002 to 20% by weight composition. Preferably, in order to lower cost and maximize the effect, the amount of resveratrol is in the range of from 0.001% to 10% and most preferably is in the range of from 0.1% to 5%.

The addition of a Krebs tricarboxylic acid cycle substrate (such as malate), optionally with a source of substrate (ketone bodies derived from the fatty acid portion of triglycerides such as tri-stearyl glycerol), can enhance the antioxidant activity of the antioxidant compounds, such as those found in green tea, chocolate and resveratrol, since the combination of a substrate such as fatty acids and a Krebs cycle intermediate such as malate can be expected to enhance the ability of the cells to generate the reducing equivalents needed to carry out antioxidant activities. As discussed above, calculations of free radical production in normal humans indicate that it is impossible to ingest enough "antioxidant" to significantly reduce the burden of free radicals produced during normal human metabolism. The "priming" of the parts of the cells that produce the reducing equivalents necessary to regenerate antioxidants is therefore critical.

Therefore, in certain preferred embodiments, fatty acids esterified to glycerol (such as stearyl glycerol), pyruvate, preferably in the form of pyruvic acid, are also an ingredient of the inventive skin care composition. Fatty acids are converted by cellular metabolism to "ketone bodies" (acetoacetic acid and β-hydroxybutyric acid) which are then converted in the mitochondria into acetyl-Coenzyme A, the main external substrate of the Krebs tricarboxylic acid cycle.

Similarly, as discussed above, pyruvate is converted to acetate during normal metabolism, and pyruvic acid ($CH_3COCO_2H$) is an alpha-keto acid which plays an important role in biochemical processes. Pyruvic acid is the output of the metabolism of glucose (glycolysis), wherein one molecule of glucose breaks down into two molecules of pyruvic acid, which are then used to provide further energy, in one of two ways. Provided that sufficient oxygen is available, pyruvic acid is converted into acetyl-coenzyme A, which is the main input for the Krebs cycle, as discussed above. Pyruvate is also converted to oxaloacetate by an anaplerotic reaction and then further broken down to carbon dioxide. Shapiro et al. discussed the use of pyruvic acid in order to promote energy production or the uptake of oxygen into the skin. In the alternative to pyruvic acid, pyruvic acid ethyl ester (ethyl pyruvate) and pyruvic acid methyl ester (methyl pyruvate) may be included in the inventive composition.

The skin care composition preferably also comprises at least one vitamin, mineral, metabolism-enhancing compound, or mixture thereof. Exemplary vitamins that are useful as an adjuvant for a skin care composition include but are not limited to Vitamin A (with carotenoids), thiamine (vitamin $B_1$), riboflavin (vitamin $B_2$), niacin (vitamin $B_3$), pantothenic acid (vitamin $B_5$, pyridoxine derivatives (vitamin $B_6$), Cyanocobalamin (vitamin $B_{12}$), Vitamin C. Vitamin A is preferred because it strengthens the protective tissue of the skin, prevents acne and helps reduce sebum production, and is thus essential for the maintenance and repair of the tissue of which the skin and mucous membranes are made. B-complex vitamins are preferred for administration as adjuvants because of their involvement with metabolism. Additional vitamins may be included, such as chromium (often in chromium picolinate or chromium polynicotinate form), which aids in reducing infections of the skin, Vitamin E, which enhances healing and tissue repair, and Vitamin K.

Exemplary minerals that are useful as an adjuvant include but are not limited to calcium, magnesium, sodium, selenium, copper, potassium and zinc.

Exemplary metabolism-enhancing compounds include L-carnitine and its derivatives, and creatine. Creatine supplementation is described in U.S. Pat. No. 5,767,159 (Hultman), which is hereby incorporated by reference. L-carnitine has been found to ameliorate abnormalities associated with Alzheimer's Disease in a model system (Malow et al., "Cultured Cells as a Screen for Novel Treatments of Alzheimer's Disease," Arch. Neurol. 46:1201-1203 (1989), which is hereby incorporated by reference).

The skin care composition further preferably comprises a material that provides a fuel ("substrate") that can be readily metabolized by skin cells to provide a material for mitochondrial oxidative metabolism. This can include but is not limited to fatty acid esters of glycrol such as tri-, di- or mono-esters of glycerol with stearic acid, palmytic acid, or other naturally occurring fatty acids including unsaturated fatty acids such as arachodonic acid, with octanoic acid, with organic acids with one carboxyl group and carbon lengths of 10-18 carbon atoms or carbon lengths of 20 or more (either saturated or unsaturated), and with the fatty acids derived from ω-3 or ω-6 unsaturated fatty acids. They can also include esters of these fatty acids with alcohols other than glycerol. They can also include esters of glycerol with dicarboxylic acids including components of the Krebs tricarboxylic acid cycle, in which either one or both carboxyl groups of the dicarboxylic acid are esterified, to either the same —OH group in a polyalcohol such as glycerol or α,β-butanediol.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

There are many types of fatty acids, but they can be divided into three groups—saturated fats, monounsaturated fats and polyunsaturated fats. Polyunsaturated fats include ω-3 and ω-6 fatty acids, among others. The unsaturated lipid of the present invention can be selected from, e.g., the group consisting of saturated, unsaturated or polyunsaturated monoglycerides, diglycerides, triglycerides, fatty acids, fatty alcohols, phosphatides, sterols, fat-soluble vitamins, terpenes and mixtures thereof. A major polyunsaturated fatty acid is arachidonic acid, which is neither ω-3 nor ω-6.

Suitable fatty alcohols and acids include those compounds having from 10 to 24 carbon atoms. Compounds such as cetyl, myristyl, palmitic and stearyl alcohols and acids are preferred. Especially preferred embodiments of the inventive skin care composition contain esters or ethers of such long-chain fatty acids, including but not limited to palmitate and stearate, as well as ω-3 and ω-6 fatty acids, among others.

Esters may be mono- or di-esters, tri-esters, or higher order esters if alcohols with more than three —OH residues are used. The preferred esters are of physiological fatty acids with glycerol, i.e. tri-stearyl glycerol or tri-palmityl glycerol. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Other acceptable esters include coco-caprylate/caprate (a blend of coco-caprylate and coco-caprate), propylene glycol myristyl ether acetate, diisopropyl adipate and cetyl octanoate.

Among the polyols which may serve as emollients are linear and branched chain alkyl polyhydroxyl compounds. A most preferred polyol is glycerol (1,2,3-propane triol). Other acceptable examples include, for example, propylene glycol, sorbitol and glycerin. Also useful may be polymeric polyols such as poly-propylene glycol and polyethylene glycol. Butylene and propylene glycol are also especially preferred as penetration enhancers.

One example of a suitable emollient that is also an excellent substrate for skin mitochondrial metabolism and that may be used for the inventive skin care composition is tristeryl glycerol (stearin), a triglyceride of stearic acid, i.e., the tristearate ester of glycerol, which is insoluble in water and very slightly soluble in alcohol, is found in many hard fats and oils, e.g., in tallow, suet, butterfat, cottonseed oil and olive oil, and is frequently used in making soap.

An oil or oily material may be present together with an emulsifier to provide either a water-in-oil emulsion or an oil-in-water emulsion, depending largely on the average hydrophilic-lipophilic balance (HLB) of the emulsifier employed. It is advisable to use a vegetable oil to allow the mixing together of the various ingredients. Particular unsaturated lipids include high oleic acid content sunflower oil, sunflower oil, rapeseed oil, soybean oil, peanut oil, canola oil, cottonseed oil, coconut oil, palm oil, palm kernel oil, corn oil, flax seed oil, olive oil, safflower oil, fish oil and mixtures thereof. Unsaturated fatty acids which include ω-3 and/or ω-6 fatty acids, such as fish oils and flaxseed oil, sunflower oil and safflower oil, are particularly preferred.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in an amount anywhere from 0.1 to 20% by weight, preferably from about 0.5% to 10% by weight of the composition. Exemplary thickeners are cross-linked polyacrylate materials available under the trademark Carbopol from the B.F. Goodrich Company. Gums may be employed such as Xanthan, carrageenan, gelatin, karaya, pectin and locust bean gum. Under certain circumstances, the thickening function may be accomplished by a material also serving as a silicone or emollient. For instance, silicone gums in excess of 10 centistokes and esters such as glycerol stearate have dual functionality.

The skin care composition may also in preferred embodiments contain relatively low concentrations of agents that are widely used in dermatology and cosmetics as debriding agents to remove dead skin, such as retinoic acid or other organic acids including 2-hydroxy acids or their esters.

Powders may also be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch, octenyl succinate and mixtures thereof.

The inventive compositions also may include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used, as can titanium dioxide, zinc oxide, avobenzone, octocrylene and melanin derivatives as well as other sunscreens derived from plant, animal and marine sources. The exact amount of sunscreen employed in the emulsions can vary depending upon the degree of protection desired from the sun's ultraviolet radiation.

Other adjunct minor components may also be incorporated into the cosmetic compositions. These ingredients may include coloring agents, opacifiers and perfumes. Amounts of these other adjunct minor components may range anywhere from 0.001% up to 20% by weight of the composition.

The composition according to the invention also comprises a cosmetically acceptable vehicle to act as a diluent, dispersant or carrier for the composition, so as to facilitate its distribution when the composition is applied to the skin. Vehicles other than or in addition to water can include liquid or solid emollients, solvents, humectants, thickeners and powders. An especially preferred nonaqueous carrier is a polydimethyl siloxane and/or a polydimethyl phenyl siloxane. Silicones of this invention may be those with viscosities ranging anywhere from about 10 to 10,000,000 mm$^2$/s (centistokes) at 25° C. Especially desirable are mixtures of low and high viscosity silicones, which are available from the General Electric Company under trademarks Vicasil, SE and SF and from the Dow Corning Company under the 200 and 550 Series. Amounts of silicone that can be utilized in the compositions of this invention range anywhere from 5% to 95%, preferably from 25% to 90% by weight of the composition.

The cosmetically acceptable vehicle will usually form from 5% to 99.9%, preferably from 25% to 80% by weight of the composition, and can, in the absence of other cosmetic adjuncts, form the balance of the composition. Preferably, the vehicle is at least 80 wt. % water, by weight of the vehicle. Preferably, water comprises at least 50 wt. % of the inventive composition, most preferably from 60 to 80 wt. %, by weight of the composition.

The nature and the quantity of these adjuvants may be selected by the specialist skilled in the art on the basis of his general knowledge so as to obtain the desired form of presentation for the composition. In any case the specialist skilled in the art will take care to choose all of optional additional compounds and/or their quantity such that the advantageous properties of the composition according to the invention are not, or not substantially, impaired by the addition considered. Except in the examples, or where otherwise explicitly indicated, all numbers in this description indicating amounts of material or conditions of reaction, physical properties of materials and/or use are to be understood as modified by the word "about". All amounts are by weight of the composition, unless otherwise specified.

Thus, the compositions according to the invention may be presented in particular in the form of: a product for the care, treatment, cleansing or protection of the skin of the face or body including the scalp, such as a care composition (daytime, nighttime, hydrating) for the face or body; an anti-wrinkle or anti-age composition for the face; a composition rendering the face mat; a composition for irritated skin; a composition for the removal of make-up; a milk for the body, in particular a hydrating milk, optionally after exposure to the sun; a sun protection composition, an artificial tanning composition (self-tanning) or care composition after exposure to the sun; a composition for the hair, and in particular a sun protection cream or gel; a care composition for the scalp, in particular against hair loss or for stimulating hair growth; antiparasitic shampooing; a product for the make-up of the skin or the face, body or lips, such as foundation make-up, complexion cream, rouge or eyelid make-up, a free or compact powder, anti-shadow stick, a camouflaging stick, a lipstick, a lip care composition; a product for buccal hygiene such as toothpaste or a mouthwash. The compositions according to the invention are preferably applicable as a facial or hand skin composition, of the anti-wrinkle or anti-age type, and as a sun protection or after sun exposure composition.

The skin treatment composition of the invention can be formulated as a lotion, a cream or a gel. The composition can be packaged in a suitable container to suit its viscosity and intended use by the consumer. For example, a lotion or cream can be packaged in a bottle, or a propellant-driven aerosol device or a container fitted with a pump suitable for finger operation. When the composition is a cream, it can simply be stored in a non-deformable bottle or squeeze container, such as a tube or a lidded jar. The invention accordingly also provides a closed container containing a cosmetically acceptable composition as herein defined.

The skin treatment method of the invention may be used in particular by applying the cosmetic compositions such as defined above according to the usual procedure for the use of those compositions. For example, if the composition is in the form of a skin cream, a small quantity of the composition, such as from 1 to 100 ml, is applied to exposed areas of the skin, from a suitable container or applicator and, if necessary, it is then spread over and/or rubbed into the skin using the hand or fingers or a suitable device.

The skin treatment composition of the invention can also be administered to the skin using a vehicle such as a patch or pad impregnated with the active ingredients that is adhered or applied to the affected areas of the skin. For example, such a vehicle could be a small pad for application of the composition to scars or seborrheic keratoses or rough spots, brown spots (lentigos and lentigines), or could be larger patches or pads for application to the forehead, crows feet or upper lip for targeting wrinkles. Such a vehicle could also be in the form of a full face masque impregnated with the active ingredients for overnight application. Such patches or pads not only enable the user to target the treatment area directly but also provide an occlusion to enhance penetration of the composition into the skin.

Because one embodiment of the skin care composition includes unesterified forms and small concentrations of carboxylic or tricarboxylic acids of Krebs cycle intermediates and precursors of Krebs cycle intermediates as skin irritants to remove (debride) dead skin, one embodiment of the invention can also be distributed in a kit along with an exfoliating implement, such as a brush, for exfoliation of the skin prior to treatment.

The invention is illustrated in more detail in the following examples, which are put forth so as to provide those of ordinary skill in the art with a complete disclosure and description of how to make and use the subject invention, and are not intended to limit the scope of what is regarded as the invention. Efforts have been made to insure accuracy with respect to the numbers used (e.g. amounts, temperature, concentrations, etc.) but some experimental errors and deviations should be allowed for. Unless otherwise indicated, parts are parts by weight, molecular weight is weight average molecular weight, temperature is in degrees centigrade, and pressure is at or near atmospheric.

EXAMPLES

The following Examples are provided to illustrate embodiments of the present invention but are by no means intended to limit its scope.

Example 1

Skin Soap

| Ingredients: | glycerin soap | 115 gm |
| | Raw chocolate, powdered | 2 tablespoons |
| | Resveratrol | ⅛ teaspoon |
| | Ethyl pyruvate | 2 tbsp |
| | Diethyl malate | 2 tbsp |

Procedure: A small sample of this skin soap was made in the following manner: Soap was melted in a double-boiler (earthenware glazed dish in a container of boiling water), and ingredients added in the order listed above. Five squirts of (Dior) eau de toilette were added, and the soap was allowed to cool and then cut out of the mold and into convenient sized pieces.

Example 2

Skin Cream

| Ingredients: | skin cream base | 250 gm |
| | Raw chocolate, powdered | 2 tablespoons |
| | Resveratrol | ¼ teaspoon |
| | Ethyl pyruvate | 3 tablespoon |
| | Diethyl malate | 3 tablespoons |
| | Eau de toilette (Dior) | 6 puffs |

Procedure: A small sample of this skin cream was made in the following manner: The cream base was melted in a double boiler, then were ingredients added with mixing in the order above. (See Example 1 for details) Mixture brought to boil in the double boiler, and cooked 1-2 minutes, until well mixed. Ingredients were stirred regularly while cooking, since the chocolate might not otherwise dissolve well in the cream base.

Clinical Testing of Examples 1 and 2

Clinical testing was done for the soap in Examples 1 and 2 over three months in a fair-skinned woman of Scandinavian origin who volunteered for this trial, and these tests proved that this preparation was unsatisfactory. While these compositions did reduce the size of age spots, they also led to local allergic skin reactions. Skin testing demonstrated that these allergic reactions were due to the diethyl malate and, to a lesser extent, to the ethyl pyruvate. When the use of the cream containing these ingredients was discontinued, the allergic lesions cleared completely without scarring.

As a result of these allergic reactions, the diethyl malate was replaced with 5 ml diethylhexyl malate, and the ethyl pyruvate was replaced with 5 gm Tristeryl Glycerol (Stearin) in the next formulations, set forth below.

Example 3

"Green Cream" Formulation

Ingredients: 5 gm Undutched raw chocolate, ground fine, partly melted in 15 ml water
5 gm Green Tea Powder, unheated, natural
1 gm Resveratrol
5 ml Diethylhexyl malate
5 gm Tristeryl Glycerol (Stearin)

The emollient cream into which the above ingredients were dissolved is a standard mixture, of an oil phase and an aqueous phase. The active ingredients were added during the formation of the emollient cream, and all were thereafter homogenized together. The sample was then passed through an ointment mill three times, with reductions in the particle size each time. This reduced the granularity of the chocolate grains to an acceptable level for a skin cream.

Clinical Testing of Example 3

Open Trial in One Individual: This development trial was carried out in one woman aged 65, a fair-skinned, blond haired lady of Scandinavian origin. The green cream was applied for two months both to "age spots" and to the middle of an old, somewhat faded surgery scar on the subject's right flank. The age spots were reduced in size and became flatter over the time of the trial period; almost half of them (23/50) disappeared permanently. In addition, the scar disappeared in the area where the cream had been applied, as monitored by several observers. The encouraging results with this one subject led to a double blind trial in eight Caucasian women, as described below.

Examples 4, 5 and 6

Additional "Green Cream" Formulations

The creams produced as Examples 4-6 were produced by wetting the powdered ingredients with the liquid ones with the addition of a 5 cc of Propylene Glycol and incorporated by EMP at 2:00/5 into the emollient cream base. Each of the samples was made with 110 gm each.

Ingredients of Example 4: The three antioxidants
5 gm Undutched Raw Chocolate ground fine and partly melted
5 gm Green Tea Powder Unheated Natural
1 Gm Resveratrol
5 cc Propylene Glycol to wet
QS (quantum sufficiat) 100 gm Emollient Base
Ingredients of Example 5: Same as Example 4 plus:
5 ml Diethylhexyl malate
5 gm Tristeryl Glycerol (Stearin)
Ingredients of Example 6: QS 100 gm Emollient Base plus Colors Upon production, it was observed that the composition of Example 4 was very gritty because the particle size of the chocolate and green tea solids was too large. It was also observed that the composition of Example 5 was not as gritty as Example 4 but could still have benefited from a smaller particle size.

It was further observed that the composition could be improved by adding the active ingredients during preparation of the cream, instead of incorporating the active ingredients into a cream base, in order to help particle size due to mild heating and be closer to the actual manufacturing procedure. In addition, the chocolate should be melted before use, and the cream should be homogenized while still in liquid form.

Examples 7, 8 and 9

Additional "Green Cream" Formulations

The creams produced as Examples 7-9 were produced with 120 gm each.

Ingredients of Example 7: Sample made with the three antioxidants per 100 gm:
5 gm Undutched Raw Chocolate ground fine and partly melted
5 gm Green Tea Powder Unheated Natural
1 Gm Resveratrol
Ingredients of Example 8: Sample made with all five active ingredients per 100 gm:
5 gm Undutched Raw Chocolate ground fine and partly melted
5 gm Green Tea Powder Unheated Natural
1 Gm Resveratrol
5 ml Diethylhexyl malate
5 gm Tristeryl Glycerol (Stearin)
Ingredients of Example 9: Sample made with all five active ingredients per 100 gm:
5 gm Undutched Raw Chocolate ground fine and partly melted
5 gm Green Tea Powder Unheated Natural
1 Gm Resveratrol
5 ml Diethylhexyl malate
5 gm Tristeryl Glycerol (Stearin)

In each of Examples 7, 8 and 9, the active ingredients were added during the formation of the cream and all the ingredients were homogenized afterwards. Because the high percentage of particulate matter caused a caking of the ingredients during the homogenization stage of Examples 7, 8 and 9, a blender was used in place of the homogenizer.

In first attempts at Examples 7 and 8, the chocolate did not melt at 50° C. and started to burn at higher temperatures. In the second attempts, after 15 ml of water was added to the chocolate prior to heating, the chocolate still did not melt but the particle size was reduced to a certain degree.

Example 9 underwent one final step: The sample was passed through an ointment mill three times reducing the setting for particle size each time. It was believed that this reduced the particle size of the active ingredients to an acceptable level.

The first attempts at Examples 7, 8 and 9 still felt somewhat pasty, as a result of the high particulate count. The solution was to use a green tea liquid extract or tincture, and to decrease the oil constituent of the emollient base. In the second attempts, the emollient mixture was altered and prepared with fewer oil constituents in order to reduce the pastiness of the cream.

Clinical Testing of Examples 7 and 8

Double Blind Comparison with and without Substrates: This double-blind, controlled trial compared the effects on skin of two forms of the "green cream", one form containing both antioxidants and mitochondrial substrates (the cream composition of Example 8), the other form containing the (same) antioxidants but without the added substrates for skin mitochondria (the cream composition of Example 7). The second form was considered the "placebo." The comparison thus tested whether or not the addition of substrates for skin mitochondrial metabolism were beneficial or whether the mixture of antioxidants alone was equally or more useful.

The subjects were eight white women aged 40 to 60 who volunteered for this trial, after having the procedures explained to them and providing written informed consent according to local standards. The duration of the study was two months, from mid-November 2005 through mid-January 2006, when the effects of sun exposure are minimal during these weeks in Eastern Pennsylvania, where the trial was carried out.

The design of the trial was double-blind, with each subject acting as her own control. Each woman used the cream with the substrates and antioxidants on the outer aspect of one forearm and the cream with only the antioxidants on the outer aspect of the other forearm. Four women used the complete cream on the right forearm, and four women used the complete cream on the left forearm. Specifically, four participants used the composition of Example 7 on the right forearm and the composition of Example 8 on the left forearm, and four participants used the composition of Example 8 on the right forearm and the composition of Example 7 on the left forearm. Neither the women nor the examiner knew which cream was being used on which forearm. The creams were applied twice daily for the duration of the study.

Outcome measures were clinical, according to a predetermined numerical scale. Values were given for erythema, pigmentation, wrinkling, and firmness/elasticity using a scale of 0 to 3 at both the beginning and end of the study. A board certified, research trained dermatologist scored the results, blind to which preparation had been used on which forearm.

Results: There were no signs of irritation, contact dermatitis or folliculitis/acne in any of the participants during the study. It was observed that six of the eight women showed more improvement on the forearm treated with the complete preparation of Example 8 (antioxidants plus substrates), one woman improved more on the forearm treated with the composition of the antioxidants alone (Example 7), and one woman showed an equal improvement on the forearms treated with the compositions of Examples 7 and 8. In all, there were 26 improvement points on the forearms treated with the complete cream (the composition of Example 8), and 18 improvement points on the forearm treated with the cream containing the antioxidants but not the metabolic substrates (the composition of Example 7). One participant had six improvement points on the forearm treated with the complete preparation (the composition of Example 8) but only one improvement point on the forearm treated with the preparation not containing substrates (the composition of Example 7). There was no such dramatic improvement point wise in any of the forearms treated with the composition of Example 7 containing antioxidants alone compared to forearms treated with the composition of Example 8 containing the complete preparation. Statistical analysis (Chi squared test) indicated that the improvement on the complete preparation (substrate and Krebs cycle intermediate as well as antioxidants) was statistically significant compared to that with the antioxidants alone (P<0.01). Therefore, in a preferred embodiment, the composition comprises a combination of a mitochondrial stimulating mixture plus a "ladder" of antioxidants rather than to an antioxidant cream alone.

Conclusions: These results have three implications.

i. The use of both creams, antioxidants alone and antioxidants with substrates, appears to benefit the skin of middle-aged, Caucasian American women.

ii. The preparation containing both added substrates and also antioxidants appeared more effective than the cream containing only (the same) antioxidants.

Example 10

Oil Based Formulation

Ingredients: 5 gm Undutched Raw Chocolate ground fine and partly melted
5 gm Green Tea Powder Unheated Natural
1 gm Resveratrol
5 ml Diethylhexyl malate
5 gm Tristeryl Glycerol (Stearin)
4 gm Cholesterol
4 gm Stearyl Alcohol
10 gm White Wax
10 gm Safflower Oil
5 gm Flaxseed Oil
White Petrolatum QS 100 gm It is understood that one skilled in the art can make obvious variations to the embodiments disclosed herein. These obvious variations are meant to be encompassed by the appended claims.

The invention claimed is:

1. A topical skin composition for stimulating mitochondrial activity in the skin cells of humans, comprising (a) a Krebs cycle intermediate, a precursor of a Krebs cycle intermediate, or a combination thereof, comprising diethylhexyl malate;
(b) a pharmaceutically acceptable topical vehicle comprising a mitochondrial fuel or substance that is efficiently convertible to mitochondrial fuel by normal skin cell metabolism comprising tristearyl glycerol, and
(c) at least one antioxidant selected from the group consisting of undutched raw chocolate, green tea and resveratrol;
wherein the combination of (a), (b) and (c) is in an amount effective to stimulate mitochondrial activity in skin cells of humans when administered to skin regions of human subjects in need thereof.

2. The topical skin composition of claim 1, further comprising at least one additional antioxidant selected from the group consisting of catechins, (−)-epicatechins, curcumin, ascorbic acid, Vitamin E, alpha-lipoic acid, α-tocopherol, dimethyl-amino-ethanol (DMAE), quercetin, flavonoids and mixtures thereof.

3. The topical skin composition of claim 1, further comprising at least two antioxidants.

4. The topical skin composition of claim 1, further comprising a vitamin, a mineral, a metabolism-enhancing compound, or a mixture thereof.

5. The topical skin composition of claim 4, wherein the vitamin is selected from the group consisting of Vitamin A, thiamine, riboflavin, niacin, pantothenic acid, pyridoxine derivatives, Cyanocobalamin, Vitamin C, chromium, Vitamin E, Vitamin K and mixtures thereof.

6. The topical skin composition of claim 4, wherein the mineral is selected from the group consisting of calcium, magnesium, sodium, selenium, copper, potassium, zinc and mixtures thereof.

7. The topical skin composition of claim 4, wherein the metabolism-enhancing compound is selected from the group consisting of L-carnitine, L-carnitine derivatives, creatine and mixtures thereof.

8. The topical skin composition of claim 1, wherein the pharmaceutically acceptable topical vehicle comprises an emollient.

9. The topical skin composition of claim 8, wherein said emollient is selected from the group consisting of esters, fatty acids and alcohols, polyols, hydrocarbons and mixtures thereof.

10. The topical skin composition of claim 9, wherein the fatty acids are selected from the group consisting of ω-3 fatty acids, ω-6 fatty acids, saturated and/or unsaturated monoglycerides, diglycerides, triglycerides, fatty acids, fatty alcohols, phosphatides, sterols, fat-soluble vitamins, terpenes, and mixtures thereof.

11. The topical skin composition of claim 9, wherein the fatty acids are selected from the group consisting of high oleic sunflower oil, sunflower oil, rapeseed oil, soybean oil, peanut oil, canola oil, cottonseed oil, coconut oil, palm oil, palm kernel oil, corn oil, flax seed oil, olive oil, safflower oil, fish oil, mineral oil, petroleum jelly, squalene, isoparaffins and mixtures thereof.

12. The topical skin composition of claim 1, further comprising at least one pharmaceutically acceptable excipient selected from the group consisting of thickeners, powders, sunscreens, coloring agents, opacifiers, perfumes, diluents, dispersants and mixtures thereof.

13. The topical skin composition of claim 1, in the form of a lotion, cream, gel, spray, pump or impregnated pad or patch.

14. The topical skin composition of claim 1, wherein the pharmaceutically acceptable topical vehicle comprising a mitochondrial fuel or substance that is efficiently convertible to mitochondrial fuel by normal skin cell metabolism is selected from the group consisting of fatty acid esters of alcohols.

15. The topical skin composition of claim 14, wherein the alcohol is chosen from the group consisting of cetyl alcohol, myristyl alcohol, palmitic alcohol and stearyl alcohol.

16. The topical skin composition of claim 14, wherein the alcohol is glycerol.

17. The topical skin composition of claim 14, wherein the fatty acid ester of alcohol is selected from the group consisting of tri-esters, di-esters or mono-esters.

18. The topical skin composition of claim 14, wherein the fatty acid is chosen from the group consisting of stearic acid, palmytic acid, and unsaturated fatty acids such as ω-3 and ω-6 fatty acids, arachodonic acid and octanoic acid.

19. The topical skin composition of claim 14, wherein the fatty acid is unsaturated.

20. The topical skin composition of claim 14, wherein the pharmaceutically acceptable topical vehicle comprising a mitochondrial fuel or substance that is efficiently convertible to mitochondrial fuel by normal skin cell metabolism is tristearyl glycerol or tri-palmityl gluycerol.

21. The topical skin composition of claim 1, wherein the undutched raw chocolate is present in an amount of about 0.00002% to about 20% by weight.

22. The topical skin composition of claim 1, wherein said green tea comprises green tea extract.

23. The topical skin composition of claim 22, wherein the green tea extract is present in an amount of about 0.00002% to about 20% by weight.

* * * * *